United States Patent [19]

Kufner-Muhl et al.

[11] Patent Number: 5,688,802
[45] Date of Patent: Nov. 18, 1997

[54] BORNYL XANTHINE DERIVATIVES WITH ADENOSINE-ANTAGONISTIC ACTIVITY

[75] Inventors: Ulrike Kufner-Muhl, Mainz; Karl-Heinz Weber, Gau-Algesheim; Gerhard Walther, Bingen; Werner Stransky, Gau-Algesheim; Helmut Ensinger, Ingelheim Am Rhein; Gunter Schingnitz, Bad Kreuznach; Franz Josef Kuhn, Gau-Algesheim; Erich Lehr, Waldalgesheim, all of Germany

[73] Assignee: Boehringer Ingelheim KG, Ingelheim am Rhein

[21] Appl. No.: 663,417

[22] Filed: Jun. 14, 1996

Related U.S. Application Data

[62] Division of Ser. No. 097,478, Jul. 27, 1993, Pat. No. 5,532,368, which is a division of Ser. No. 942,871, Sep. 10, 1992, abandoned, which is a continuation of Ser. No. 691,193, Apr. 25, 1991, Pat. No. 5,175,291, which is a continuation of Ser. No. 452,643, Dec. 18, 1989, abandoned.

[30] Foreign Application Priority Data

Dec. 22, 1988 [DE] Germany ............... 38 43 117.3

[51] Int. Cl.$^6$ ............... C07D 473/06; A61K 31/52
[52] U.S. Cl. ............... 514/263; 544/267
[58] Field of Search ............... 544/264, 265, 544/267; 514/263

[56] References Cited

U.S. PATENT DOCUMENTS

| | | | |
|---|---|---|---|
| 5,175,291 | 12/1992 | Kufner-Muhl | 544/267 |
| 5,447,933 | 9/1995 | Suzuki et al. | 514/263 |
| 5,525,607 | 6/1996 | Suzuki et al. | 544/267 |

*Primary Examiner*—Mukund J. Shah
*Assistant Examiner*—Pavanaram K. Sripada
*Attorney, Agent, or Firm*—Robert P. Raymond; Wendy E. Rieder; Alan R. Stempel

[57] ABSTRACT

The invention relates to new xanthine derivatives of general formula I, processes for preparing them and their use as pharmaceutical compositions.

3 Claims, No Drawings

BORNYL XANTHINE DERIVATIVES WITH ADENOSINE-ANTAGONISTIC ACTIVITY

This is a division of application Ser. No. 08/097,478, filed Jul. 27, 1993, now U.S. Pat. No. 5,532,368 which is a division of application Ser. No. 07/942,871, filed Sep. 10, 1992, now abandoned which is a continuation of application Ser. No. 691,193, filed Apr. 25, 1991, now U.S. Pat. No. 5,175,291 which is a continuation of application Ser. No. 452,643, now abandoned.

The invention relates to new xanthine derivatives processes for preparing them and their use as pharmaceutical compositions.

The new xanthines have the structure of general formula I

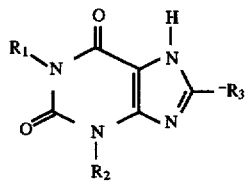

wherein $R_1$ is a $C_{1-6}$, preferably $C_{1-4}$ alkyl group, a $C_3$ or $C_4$ alkenyl group or a $C_3$ or $C_4$ alkynyl group;

$R_2$ is a $C_3$ or $C_4$ alkenyl group, a $C_{1-6}$, preferably $C_{1-4}$ alkyl group, an optionally substituted benzyl group or a $C_3$ or $C_4$ alkynyl group;

$R_3$ represents a C-linked saturated or unsaturated five, six or seven-membered heterocyclic ring which contains one or more heteroatoms selected from the group comprising oxygen and sulphur and may optionally carry one of the following groups:

$C_{1-6}$, preferably $C_{1-4}$ alkyl, =O, —CHO, —CH$_2$OR$_4$, —CH$_2$OR$_7$, COOR$_4$, CONR$_5$R$_6$, whilst a furan or thiophene group may also contain one of the groups —CH=CH—CONR$_5$R$_6$, —CH=C (COOR$_4$)$_2$ (R$_4$ being identical or different),

—CH=C (COOR$_4$) (CONR$_5$R$_6$),

—CH=C (COOR$_4$) (CH$_2$OR$_4$) (R$_4$ being identical or different),

—CH=C (COOR$_4$) (CH$_2$OR$_7$),

—CH=C (CH$_2$OR$_4$)$_2$,

—CH=C (CH$_2$OR$_7$)$_2$,

—CH=C (CONR$_5$R$_6$) CH$_2$OR$_4$,

—CH=C (CONR$_5$R$_6$) CH$_2$OR$_7$ or nitro and the tetrahydrofuran group may also carry a group —(CH$_2$)$_2$— CONR$_5$R$_6$;

$R_3$ represents a $C_{4-8}$ cycloalkene which may be substituted by $C_{2-4}$ alkenyl, $R_3$ represents a $C_{4-8}$, preferably $C_5$ and $C_6$, cycloalkanone or a $C_4$ to $C_8$, preferably $C_5$ and $C_6$ cycloalkanol, which may be substituted in the α-position by $C_{2-6}$, preferably $C_{2-4}$, alkenyl, $C_{2-6}$, preferably $C_{2-4}$ alkynyl, optionally substituted benzyl, CH$_2$OR$_4$, CH$_2$COOR$_7$ or (CH$_2$)$_2$CN, $R_3$ represents a $C_3$ to $C_8$, preferably $C_5$ or $C_6$ cycloalkane, which may optionally be substituted by $C_{1-6}$, preferably $C_{1-4}$ alkyl, =CH$_2$, =N—NH-aryl, preferably =N—NH-phenyl, wherein the aryl or phenyl group may be substituted, =N—NH—C$_1$ to $C_6$ alkyl, =NOH, —OCONH-aryl, preferably —OCONH-phenyl, wherein the aryl or phenyl group may be substituted, OCONH-C$_{1-6}$ alkyl, —OR$_4$, —OR$_7$, —(CH$_2$)$_1$—COOR$_4$, —(CH$_2$)$_1$— NR$_4$R$_4$ (R$_4$ being identical or different), —(CH$_2$)$_1$— CONR$_5$R$_6$, —(CH$_2$)$_1$—OR$_4$, —(CH$_2$)$_1$—OR$_7$, wherein 1 represents one of the numbers 0, 1, 2, 3 or 4, or a group =CAH wherein A represents COOR$_4$, CN, CONR$_5$R$_6$, CH=CH—COOR$_4$, CH=CH—CONR$_5$R$_6$, CH$_2$OR$_4$ or CH$_2$OR$_7$, or the cycloalkane is substituted by $C_{1-6}$, preferably $C_{1-4}$ alkyl, vinyl, allyl, optionally substituted phenyl, optionally substituted $C_{1-4}$ alkylphenyl, and has as a second substituent a hydroxyl group in a geminal position relative to the first substituent;

$R_3$ forms together with the cycloalkane a ketal of general formula

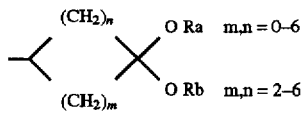

wherein

Ra represents $C_{1-4}$ alkyl and

Rb represents $C_{1-4}$ alkyl or Ra and Rb together form a $C_{2-3}$ alkylene group which may optionally be mono-or disubstituted by $C_{1-5}$ alkyl, $C_{1-5}$ alkyloxycarbonyl, hydroxy $C_{1-5}$ alkyl, preferably hydroxymethyl;

$R_3$ represents an optionally substituted group of the formula

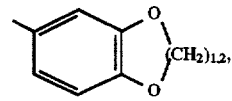

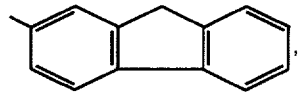

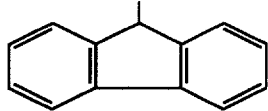

$R_3$ represents a group of formula

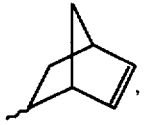

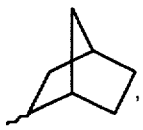

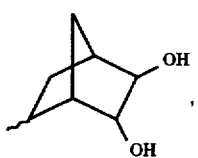

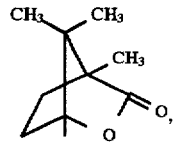

-continued

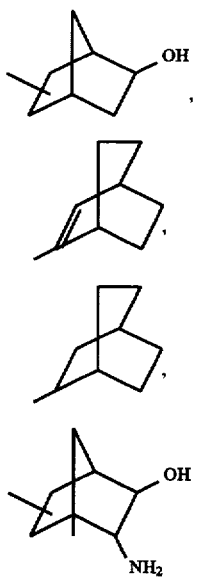

$R_4$ represents hydrogen, a $C_{1-13}$, preferably $C_{1-6}$ and $C_{11-13}$ alkyl group, an optionally substituted $C_{3-6}$ cycloalkyl group, an optionally substituted benzyl group, a $C_{3-13}$, preferably $C_{3-6}$ alkenyl, a propargyl group, a trityl group, $R_5$ represents hydrogen, a $C_{1-6}$, preferably $C_{1-4}$ alkyl group, an optionally substituted $C_{3-6}$ cycloalkyl group;

$R_6$ represents hydrogen, a $C_{1-6}$, preferably $C_{1-4}$ alkyl group, an optionally substituted benzyl group, a group of general formula —$(CH_2)_n$—$NR_5R_5$,
—$((CH_2)_n$—O—$(CH_2)_m$—$O)_k$—$(CH_2)_n$—$NR_5R_5)$
(wherein $R_5$ is identical or different) wherein n=2, 3, 4, 5, 6, 7 or 8, m=2, 3, 4, 5 or 6 and k=0 or 1,

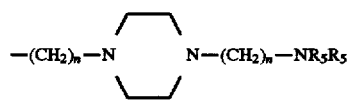

(wherein $R_5$ is identical or different), whilst the piperazine ring may be substituted by $C_{1-4}$ alkyl, preferably methyl, a C-linked piperidinyl group which is optionally substituted by $C_{1-4}$ alkyl or an N-linked benzyl group or $R_5$ and $R_6$ together with the nitrogen atom form an optionally $C_{1-4}$-alkyl-substituted five or six or seven-membered ring which may contain a further heteroatom selected from the group comprising oxygen, sulphur and nitrogen, whilst the nitrogen atom may be substituted by the group $R_4$;

$R_7$ represents an amino acid group, linked via the carbonyl function of a naturally occurring amino acid, CO—$C_1$-$C_{13}$-alkyl, preferably CO—$C_2$-$C_4$-alkyl, menthoxyacetyl, a camphanic acid group linked via a carbonyl group, abietinoyl, 4-aminobutyroyl, optionally substituted benzoyl, preferably trimethoxybenzoyl, a group of general formula CO—B, wherein B is an optionally substituted C-linked, 5, 6 or 7 membered heterocyclic group, and optionally the racemates, optically active compounds and pharmacologically acceptable acid addition salts thereof.

Preferred compounds of general formula I are those wherein $R_1$ represents an unbranched $C_{3-4}$ alkyl group, an allyl or a propargyl group;

$R_2$ represents an allyl group, a $C_{3-4}$ alkyl group or a propargyl group;

$R_3$ represents a group selected from among furan, tetrahydrofuran, tetrahydrofuranone, thiophene, dithiol, dithian or tetrahydropyran which may carry one of the following substituents: methyl, ethyl, propyl, butyl, CHO, $CH_2OR_4$, $CH_2OR_7$, $COOR_4$, $CONR_5R_6$, $R_3$ represents a furan substituted by —CH=CH—$CONR_5R_6$, —CH=C $(COOR_4)_2$ ($R_4$ being identical or different), —CH=C $(COOR_4)$ $(CONR_5R_6)$, —CH=C $(COOR_4)$ $(CH_2OR_4)$ ($R_4$ being identical or different), —CH=C $(COOR_4)$ $(CH_2OR_7)$, —$(CH_2)_n$—$CONR_5R_6$, —CH=C $(CH_2OR_4)_2$, —CH=C $(CH_2OR_7)_2$, —CH=C $(CONR_5R_6)$ $CH_2OR_4$ or —CH=C $(CONR_5R_6)CH_2OR_7$;

$R_3$ represents a cyclopentanyl or cyclohexanyl group, optionally substituted by methyl, ethyl, propyl, isopropyl, tert-butyl, allyl, vinyl, phenyl or benzyl, whilst a hydroxy group may be present as a geminal substituent;

$R_3$ represents a cyclopentanyl or cyclohexanyl group, substituted by hydroxy, methoxy, ethoxy, propyloxy, trimethoxycarbonyl, isopropyloxy, optionally substituted benzyloxy, allyloxy, propargyloxy, —$CH_2$—$CH_2$—OH, —$CH_2$—$COOCH_3$, =CH—$COOCH_3$, =C—CN, —$(CH_2)_2NH_2$=N—$NH_2$ =$CH_2$,

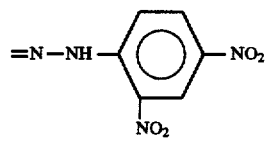

=NOH, —$CH_2OH$, $OR_4$ wherein $R_4$=methyl or trityl, OR wherein R; represents $COCH_3$, $COC_2H_5$, $COC_3H_7$, CO tert-butyl, —CO-phenyl or $COCH_2$-phenyl, optionally substituted, CO-pyridyl, —CO-(N-methyl-4H-pyridyl), —CO-(methylpyridyl), —$COCH_2$—CH=$CH_2$, —CO $CH_2$—C=CH;

$R_3$ represents a group

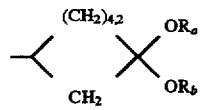

wherein $R_a$, $R_b$=$CH_3$, $C_2H_5$ or $R_a$ and $R_6$ together represent —$CH_2$—$CH_2$—, $R_3$ represents a cyclopentanone or cyclohexanone, $R_3$ represents a cycloalkane or cycloalkene with 4–8 carbon atoms, which may optionally be substituted by a straight-chained or branched $C_{2-4}$ alkenyl group; a cyclopentanone or cyclopentanol or cyclohexanone or cyclohexanol which may be substituted in α-position with respect to the keto or hydroxy group by $C_{2-4}$ alkenyl, $C_3$ or $C_4$ alkynyl, benzyl, —$CH_2CH_2CN$, $(CH_2)_3NR_5R_5$ (wherein $R_5$ is the same or different), $CH_2COOR_4$, or $CH_2OR_4$, wherein $R_4$ may represent hydrogen, methyl, ethyl or propyl;

$R_3$ represents norbornane or norbornene, optionally substituted,

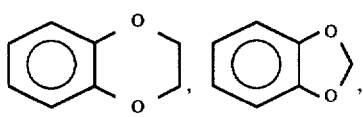

$R_4$ represents hydrogen, a $C_{1-3}$ alkyl, a cyclopropyl group, a cyclopentyl group, benzyl, an aryl group, a propargyl group or a triphenylmethyl group;

$R_5$ represents hydrogen, a $C_{1-3}$ alkyl group; a cyclopropyl group or a benzyl group;

$R_6$ represents hydrogen, methyl, ethyl, propyl, —$(CH_2)_n$—$NH_2$ (n=2–8), —$(CH_2)_n NET_2$ (n=2,3) or —$(CH_2)_3$—O—$(CH_2)_4$—O—$(CH_2)_3$—$NH_2$, N-benzyl-piperidin-4-yl, or $R_5$ and $R_6$ together with the nitrogen atom represent a piperidine, piperazine or morpholine group which may optionally be substituted by a $C_{1-4}$ alkyl group, preferably methyl;

$R_7$ represents prolinoyl, CO-$(CH_2)_{0-3}$—$CH_3$, (−)-menthoxyacetyl, a camphanic acid group linked via a carbonyl group, abietinoyl, benzoyl, 4-aminobutyroyl, 3,4,5-trihydroxybenzoyl, 3,4,5-trimethoxybenzoyl, a nicotinic acid, isonicotinic acid or picolinic acid group, an N-methylnicotinic acid group or an N-methyl-4H-nicotinic acid group, and optionally the acid addition salts thereof.

Particularly preferred compounds are the compounds of general formula I wherein $R_3$ forms an optionally substituted cyclopentane group in which the substituent is in the 3-position of the cyclopentane ring. It is particularly preferred for the group $R_3$ to represent 3-oxocyclopentane.

Examples of alkyl groups, including those which are constituents of other substituents, include methyl, ethyl, propyl, isopropyl, butyl, sec.-butyl, isobutyl, tert.-butyl, pentyl, isopentyl, neopentyl, hexyl, isohexyl and examples of longer-chained alkyl groups include decanyl, undecanyl, dodecanyl and tridecanyl and the isomers thereof. Examples of alkenyl groups include allyl (provided that it does not form any enamines), propenyl, isopropenyl, butenyl and isobutenyl. (Et=ethyl).

Examples of cycloalkyl groups include cyclopropyl, cyclobutyl, cyclopentyl or cyclohexyl which may be substituted by $C_{1-4}$ alkyl. A benzyl group, like a phenyl group, may be mono or polysubstituted by $C_{1-4}$ alkyl, preferably methyl, or by $C_{1-4}$ alkoxy, preferably methoxy, or by hydroxy and/or halogen such as fluorine, chlorine or bromine.

The term "aryl" indicates an aromatic ring system with 6 to 12 carbon atoms which may optionally be substituted by $C_{1-4}$ alkyl, halogen, hydroxy, nitro, $C_{1-4}$ alkoxy, amino, $C_{1-4}$ alkylamino and/or $C_{1-4}$ dialkylamino; the preferred aryl group is phenyl.

Examples include:

2-chlorophenyl, 2-bromophenyl, 3-fluorophenyl, 2,3-dichlorophenyl, 4-hydroxyphenyl, 2-methylphenyl, 4-methylphenyl, 3-ethylphenyl, 4-propylphenyl, 4-isopropylphenyl, 4-butylphenyl, 4-tert.-butylphenyl, 4-pentylphenyl, 2,4-dimethylphenyl, 2-trifluoromethylphenyl, 3-trifluoromethylphenyl, 2-methoxyphenyl, 4-methoxyphenyl, 3-ethoxyphenyl, 2-propoxyphenyl, 4-butoxyphenyl, 2,4-dimethoxyphenyl, 3,4,5-trimethoxyphenyl, 2,4-dinitrophenyl, 4-nitrophenyl.

Examples of cyclic groups of general formula $NR_5R_6$ include: pyrrol, pyrroline, pyrrolidine, 2-methylpyrrolidine, 3-methylpyrrolidine, piperidine-optionally mono- or polysubstituted by $C_{1-4}$ alkyl, piperazine, N-methylpiperazine, N-ethylpiperazine, N-n-propylpiperazine, N-benzylpiperazine, morpholine, thiomorpholine, imidazole, imidazoline, imidazolidine, pyrazole, pyrazoline, pyrazolidine in which the above-mentioned heterocyclic group may also be substituted by $C_{1-4}$ alkyl, preferably methyl.

Examples of heterocyclic groups which may be linked via a carbon atom include thiophene, 2-methylthiophene, 2-nitrothiophene, furan, 2-nitrofuran, tetrahydrofuran, 2-methyltetrahydrofuran, 2-hydroxymethylfuran, tetrahydrofuranone, γ-butyrolactone, α-pyran, γ-pyran, 1,3-dioxolan, 1,2-oxathiolan, 1,2-oxathiepan, tetrahydro-pyran, thiolan, 1,3-dithian, 1,3-dithiolan, 1,3-dithiolene and furfural, in which the heterocyclic group may be substituted as specified in the definitions.

Examples of heterocyclic groups which may be linked via a carbon atom and contain at least one nitrogen atom include: pyridine, pyrrol, pyrroline, pyrrolidine, piperidine, piperazine, morpholine, thiomorpholine, imidazole, imidazoline, imidazolidine, pyrazole, pyrazoline, pyrazolidine, in which the above-mentioned heterocyclic groups may be substituted by $C_{1-4}$ alkyl.

Examples of naturally occurring amino acids include alanine, valine, leucine, isoleucine, proline, phenylalanine, tryptophane, methionine, glycine, serine, threonine, cysteine, tyrosine, asparagine, glutamine, histidine, arginine, lysine.

The compounds according to the invention are adenosine antagonists; in particular they have a high affinity (up to 1.6 nM) for the $A_1$-receptor and a high selectivity for this receptor subtype.

In hippocampal slices the substances antagonise the adenosine-induced suppression of the population spikes after electrical stimulation. In vivo, an increased acetylcholine content can be detected in the rat's brain.

These results indicate that the xanthine derivatives described intensify the natural cell activity of cholinergic neurones in the brain and thus prove to be functional cholinomimetics with a central attack. EEG investigations on cats indicate a significant increase in vigilance.

Substances of this kind are of great interest for the symptomatic treatment of degenerative diseases of ageing such as senile dementia and Alzheimer's disease.

The high receptor affinity should make it possible to use low doses for treatment so that there are virtually no side effects which cannot be put down to the blocking of adenosine receptors. Similarly, because of the high $A_1$ selectivity of the compounds, $A_2$-dependent side effects should not occur. In addition to being used as geronto-psychoactive drugs and nootropics, the adenosine antagonists described could also be used to treat cardiac and circulatory disorders.

Other possible indications are degenerative diseases such as organic brain syndrome, Parkinson's disease, traumatic CNS damage, post/neurological deficit, respiratory depression (intoxication, post op) and neonatal brain damage.

Pharmacological results are shown in Table Ia. The test methods correspond to those recited in the following literary references:

Lohse M. J., V. Lenschow and U. Schwabe (1984) Mol. Pharmacol. 26, 1–9;

Virus, M. R., T. Baglajewski and M. Rachelovacki (1984) Neurotiology of Agenig 5, 61–62;

Daly, J. W., W. Padgett, M. T. Shamin, P. Butts-Lamb and J. Waters (1985) J. Med. Chem. 28, 487–492;

Bruns, R. F., G. H. Lu and T. A. Pugsley (1986) Mol. Pharmacol. 29, 331–346

TABLE Ia

| Examples according to Table I | $K_i$ [nMol] $(A_1)$ |
|---|---|
| 22 | $8 \cdot 10^{-9}$ |
| 24 | $3 \cdot 10^{-9}$ |
| 28 | $6 \cdot 10^{-9}$ |
| 33 | $3 \cdot 10^{-9}$ |
| 39 | $4 \cdot 10^{-9}$ |
| 40 | $2 \cdot 10^{-9}$ |
| 45 | $2 \cdot 10^{-9}$ |
| 49 | $2 \cdot 10^{-9}$ |
| 50 | $2 \cdot 10^{-9}$ |

The compounds according to the invention may be prepared by analogous methods known per se.

In general, 8-substituted 1,3-dialkylxanthines are obtained by reacting 1,3-dialkyldiaminouracils with aldehydes, carboxylic acids or carboxylic acid chlorides or by reacting 1,3-dialkyl-6-amino-5-nitrosouracils with aldehydes.

5,6-Diamino-1,3-dimethyluracil is commercially obtainable; derivatives substituted with other groups are prepared by reacting the corresponding dialkylurea with cyanoacetic acid with subsequent nitrosation and optional hydrogenation or reduction with dithionite to obtain the diamine (J. Org. Chem. 16, 1879 (1951) and Can. J. Chem. 46, 3413 (1968)).

$H_2N$—$CH_2$—$R_3$, followed by nitrosation and cyclisation (see 2. Med. Chem. 32, 1231 (1989)).

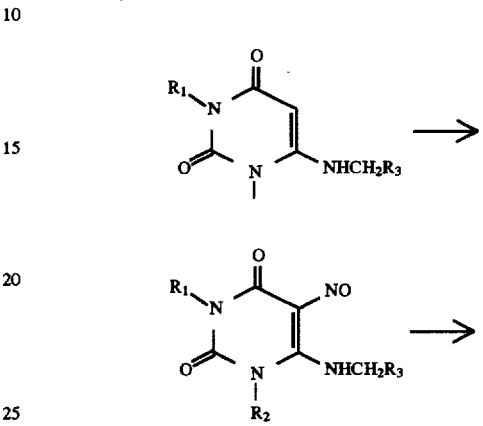

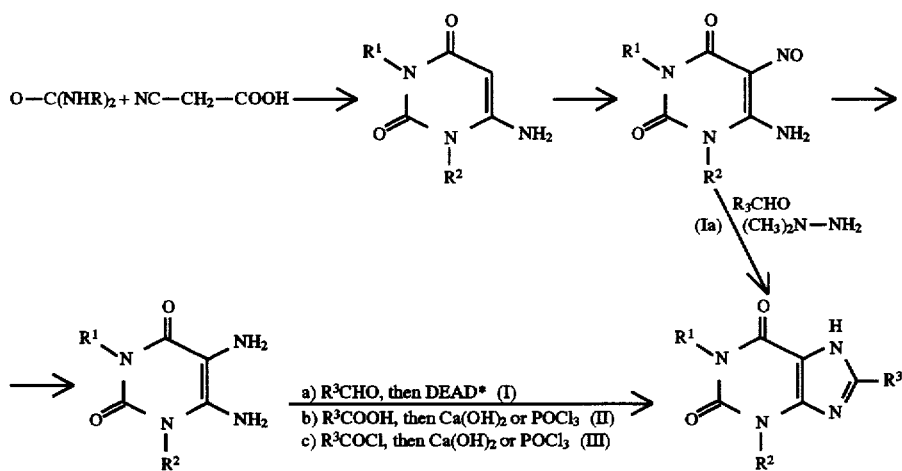

\* Diethylazodicarboxylate (The Roman numerals refer to the operating procedures described in the experimental section)

Xanthines with a benzyl group in the 3-position and a different group in the 1-position are obtained by 1-alkylation of corresponding precursor molecules which are substituted in the 3-position with a benzyl group and in the 8-position accordingly.

These can be obtained by reacting monobenzylurea and cyanoacetic acid to produce 6-amino-1-benzyluracil (L.-F. Tietze and Th. Eicher, Reaktionen und Synthesen, Georg Thieme Verlag, Stuttgart 1981, p. 322), alkylation with the desired group in the 3-position (XIV), nitrosation of the 5-position (XV) and hydrogenation to yield the 3-substituted 1-benzyl-5,6-diaminouracil (XVI). Aldehydes, carboxylic acids and acid chlorides used for the reaction with 5,6-diaminouracils can be prepared by methods known from the literature.

In suitable cases, the xanthines described may be produced by reacting 1,3-dialkyl-6-chlorobarbituric acids with -continued

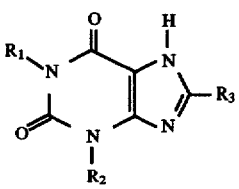

Using the processes thus described, it is possible to prepare xanthine derivatives in which $R_3$ has the following meaning, for example:

Thiophene, 2-methylthiophene, 2-nitrothiophene, furan, cyclohexan, cyclohexanone, tetrahydrofuranone, 1,3-dithiane, pyran, cyclobutane, cyclohexan, norbornene and others, provided that the corresponding aldehydes $R_3CHO$, carboxylic acids $R_3COOH$ or reactive derivatives thereof, already functionalised, can be reacted with the corresponding diaminouracil.

Other synthetic variations can then be effected on the "basic xanthine structures" thus obtained.

If desired, reactive functional groups can be protected in the usual way, starting from the corresponding 8-cycloalkanones, the corresponding alcohols may be prepared by reduction and can then in turn by esterified with carboxylic acids or acid chlorides or reacted with isocyanates to form carbamates. By reacting the corresponding ketones with hydroxylamines the corresponding oximes may be obtained, or, with substituted hydrazines, the corresponding hydrazones. The ketone function can be ketalised with alcohols in the usual way. Reduction of the ketals—for example using LiAlH$_4$/AlCl$_3$—yields the corresponding ethers. (In all the formulae which follow the positions of the groups are given solely by way of example without restricting the compounds according to the invention to the positions specified).

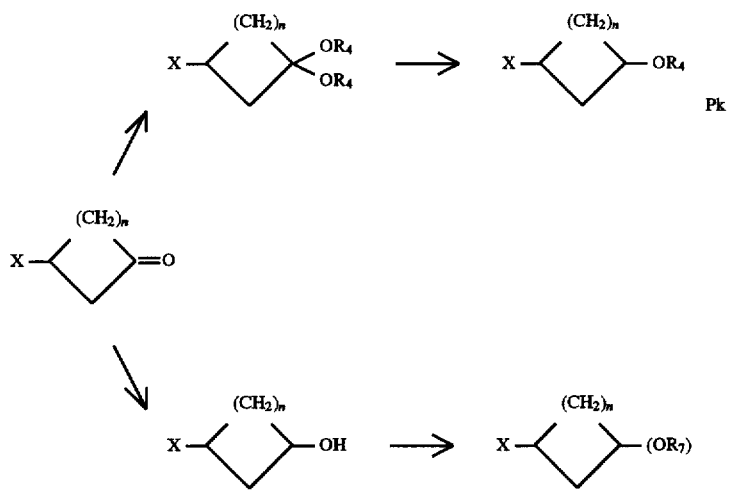

n = 1–5 ; X = "xanthine"

Wittig-Horner reactions on the ketone functions with phosphonic acid esters result in substituted olefins. By esterification of the carboxyl groups, amide formation and reduction to yield the alcohol with subsequent esterification or etherification, substituted compounds of the type specified below can be obtained, and these can subsequently be subjected to hydrogenation.

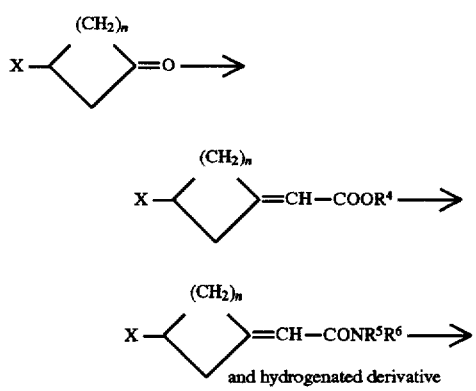

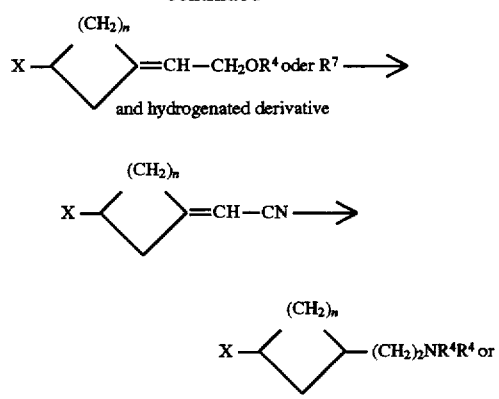

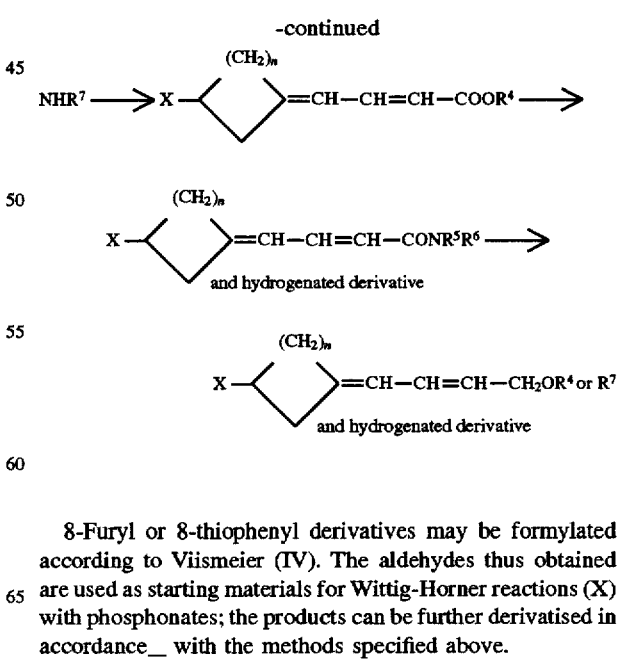

8-Furyl or 8-thiophenyl derivatives may be formylated according to Viismeier (IV). The aldehydes thus obtained are used as starting materials for Wittig-Horner reactions (X) with phosphonates; the products can be further derivatised in accordance__ with the methods specified above.

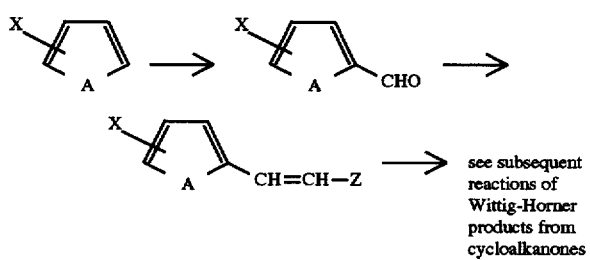

A = O, S; Z = extracting group, X = xanthine

The aldehydes are suitable for Knoevenagel reactions (XI) with malonic esters. The ester groups may be reduced to form alcohols and these may be esterified or etherified. Saponification of one of the ester groups yields the monocarboxylic acid. This serves as a starting material for the synthesis of "mixed-functional" derivatives. Thus, the combinations of ester (amide, alcohol (including esterified or etherified)/carboxylic acid, alcohol (including esterified or etherified)/amide, alcohol (including esterified or etherified) /ester, mixed ester may be obtained.

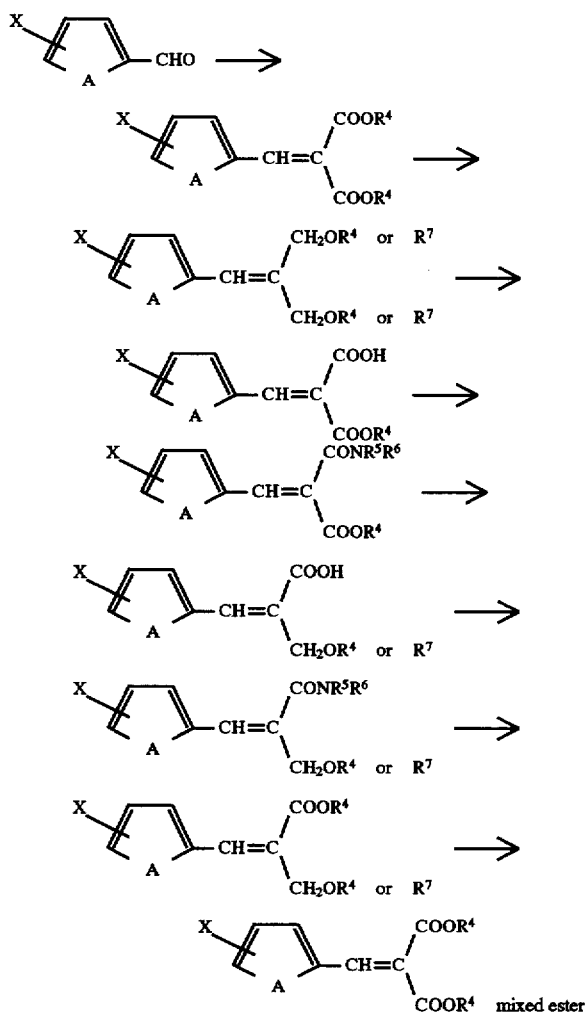

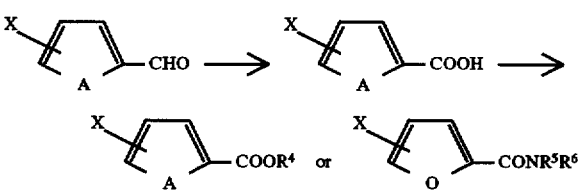

X = xanthine
A = O, S;

By reduction, the corresponding alcohols, which may be esterified and etherified, are obtainable from the aldehydes.

Reactions of oxidation yield carboxylic acids which may in turn be converted into the esters and amides.

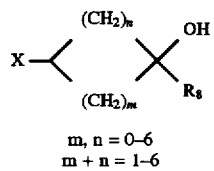

The double bond in 8-norbornenyl derivatives may be converted by reaction with $KMnO_4$ to yield the cis-diol. Reaction with m-chloroperbenzoic acid yields the epoxide which can be opened to yield the trans-diol, reacted with sodium azide to form the azido alcohol or reduced with lithium tetrahydridoalanate to yield the corresponding alcohol. The α-amino alcohol can be obtained by hydrogenation.

Starting from xanthine derivatives wherein $R_3$ represents a cycloalkanone, derivatives of general formula $$X - \underset{(CH_2)_m}{\overset{(CH_2)_n}{\diagdown}} \underset{R_8}{\overset{OH}{\diagup}}$$

m, n = 0–6
m + n = 1–6 wherein $R_8$ represents methyl, ethyl, butyl, tert.-butyl, vinyl, phenyl and benzyl, are obtained by Grignard reaction or by reacting with Li-organic reagents.

The above-mentioned cycloalkanones may be converted with the so-called Nozaki-Lombardo reagent into the corresponding methylene derivatives which can subsequently be reduced to yield the methyl compounds (J. Org. Chem. 50 (8), 1212 (1985) or after hydroboration with $BH_3$—$CH_3SCH_3/H_2O_2$, $OH^-$ yield the hydroxymethyl derivatives.

Reduction of the carbonyl group in optionally substituted cycloalkanones, e.g. using sodium tetrahydridoboranate, produces the corresponding alcohols which can be esterified or etherified in the subsequent reaction steps. Enantiomerically pure xanthine derivatives which carry a cyclopentane group as the substituent $R_3$ may be prepared according to the following plan:

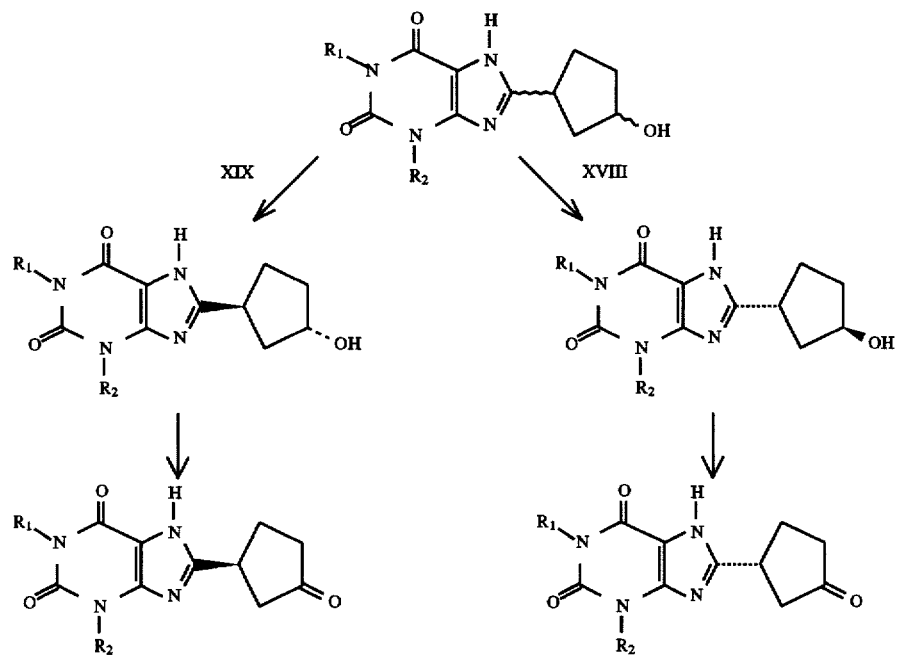

The general procedures XVIII and XIX contain other details of stereospecific synthesis.

1,3-Dipropyl-8-[3-hydroxycyclopentyl]xanthine is esterified enantioselectively with lipases in organic solvents. By subsequent purification of the residual alcohol, according to the same process the (−)-rotatary enantiomer is obtained with a purity of more than 99.5%.

Reductive cleavage of the acetate first obtained using lithium aluminium hydride yields the optically enriched (+)-alcohol, which is obtained with an enantiomeric purity of more than 99.9% by reacting with a second lipase. From these optically pure substances a whole range of optically active xanthine derivatives can be obtained with substituted cyclopentane groups in the 8-position using the methods specified.

Suitable compounds according to the invention may be converted into the acid addition salts thereof using methods known per se.

Acids suitable for salt formation include for example hydrochloric, hydrobromic, hydriodic, hydrofluoric, sulphuric, phosphoric, acetic, propionic, butyric, caproic, valetic, oxalic, malonic, succinic, maleic, fumaric, lactic, tartaric, citric, malic, benzoic, p-hydroxybenzoic, p-aminobenzoic, phthalic, cinnamic, salicylic, ascorbic and methanesulphonic acid, 8-chlorotheophylline and the like.

The preferred acid addition salts are the hydrochlorides and hydrobromides.

General Procedure I: Cyclisation with Aldehyde

Example 1

1,3-Dipropyl-8-11,4-benzodioxan-6-yl)xanthine 2.18 g (0.013 mol) of 1,4-benzodioxan-6-aldehyde, 80 ml of ethanol and 2.4 ml of glacial acetic acid are mixed together and 2.8 g (0.012 mol) of 5,6-diamino-1,3-dipropyluracil are added thereto. The clear solution is refluxed for 2¼ hours and then cooled to 60° C. At this temperature, 2.1 ml (0.013 mol) of diethylazodicarboxylate are added dropwise and the viscous suspension produced is mixed with 80 ml of ethanol and refluxed for 2 hours. After a further 20 hours at ambient temperature the mixture is cooled to 5° C., the solid matter is filtered under suction and washed with ethanol and ether. 4.1 g of the title compound are obtained in the form of a grey solid (=92% of theory), melting point 280°–282° C.

General procedure Ia: Cyclisation with Aldehydes

Example 1a

1-Propyl-3-benzyl-8-(1,4-benzodioxan-6-yl)xanthine 2.9 g (0.01 mol) of 1-benzyl-3-propyl-5-nitroso-6-aminouracil are added to 60 ml of dimethylformamide together with 2.3 g (0.014 mol) of 1,4-benzodioxan-6-aldehyde, then 0.5 g (0.014 mol) of 1,1-dimethylhydrazine are added and the mixture is refluxed for 8 hours. After working up in the usual way, the crystalline residue is triturated with ethanol and filtered under suction. 1.0 g of the title compound is obtained in the form of yellow crystals, m.p. 290° C.

General Procedure II: Cyclisation with Carboxylic Acid

Example 2

1,3-Dipropyl-8-(tetrahydropyran-4-yl)xanthine 3.2 g (0.025 mol) of tetrahydropyran-4-carboxylic acid, 4.0 g (0.025 mol) of carbonyldiimidazole and 85 ml of absolute methylene chloride are stirred for 30 minutes at ambient temperature. After the addition of 5.7 g (0.025 mol) of 5,6-diamino-1,3-dipropyluracil, the mixture is stirred for 4 hours at ambient temperature and then evaporated down in vacuo. The residue is combined with 130 ml of water and 11.6 g of calcium hydroxide, stirred for 30 minutes at 80° C. and, after cooling, acidified with conc. HCl whilst cooling with ice. The mixture is extracted with ethyl acetate and the organic phase is dried and evaporated. Chromatography of the crystalline residue on silica gel ($CH_2Cl_2/CH_3OH$ 99:1) yields 1.7 g of the title compound in the form of white crystals (15% of theory), m.p. 171°–172° C.

Example 2a

1,3-Dipropyl-8-(3-oxocyclopentyl)-xanthine 2.4 g (0.014 mol) of 1,4-dioxaspiro[4.4]nonan-7-carboxylic acid are dissolved in 56 ml of methylene chloride and after the addition of 2.2 g (0.014 mol) of carbonyldiimidazole stirred for 1 hour at ambient temperature. Then 3.2 g (0.014 mol) of 5,6-diamino-1,3-dipropyluracil are added and the mixture is stirred for a further 4 hours at ambient temperature. The solution is evaporated down in vacuo, the oily residue is mixed with 70 ml of water and 4.5 g of $Ca(OH)_2$ and stirred for 1 hour at 70° C. 100 ml of 50% NaOH are added, the mixture is stirred for a further hour at 70° C. and for 16 hours at ambient temperature. Whilst being cooled with ice, the solution is adjusted to pH 6 with HCl and extracted with methylene chloride. After drying and evaporation in vacuo the combined organic phases yield a crystalline residue which is recrystallised from ethanol using activated charcoal. 0.8 g (16%) of white crystals are obtained, m.p. 147°–148° C.

The dioxolan protecting group is then hydrolysed with acid in the manner known from the literature and the title compound is obtained.

Example 2b

1,3-Dipropyl-8-(3-oxocyclopentyl)-xanthine a) Preparation of 3-oxo-cyclopentane carboxylic acid 100.0 g of Methyl-3-oxocyclopentane carboxylate (0.7 mol) are mixed with 1000 ml of 2-molar hydrochloric acid and stirred for 10 hours at boiling temperature. The solution is cooled and fully concentrated by evaporation in vacuo. The residual water is drawn off 3 times with 50 ml of toluene each time (toluene is added to the residue and distilled off using a Rotavapor under a full water-jet vacuum and at a water bath temperature of 60°–70° C.). The crude yield is fractionally distilled in a high vacuum.

1st fraction: $Bp_{0.02}$20°–110° C. (yield: 1.2 g of oil)
2nd fraction: $Bp_{0.02}$110°–116°
yield: 4.7 g of partly crystalline oil
3rd fraction: $Bp_{0.02}$ 116°–121° C.
yield: 74.0 g of colourless oil which later crystallised out.
Yield 74.0 g (82.1% of theory)

8.8 g of 3-oxocyclopentane carboxylic acid (0.072 mol) are placed in 240 ml of absolute methylene chloride and at 20°–25° C., with stirring, 11.6 g of carbonyldiimidazole are added and the resulting mixture is stirred for 2 hours at ambient temperature. The reaction mixture is evaporated to dryness in vacuo. The oily residue is mixed with 3200 ml of distilled water and 35 g of calcium hydroxide and stirred at 80° C. for 0.5 hours. It is then cooled to 5° C. and adjusted to pH 1-2 using conc. hydrochloric acid and extracted 3 times, each time with 100 ml of $CH_2Cl_2$. The combined organic phases are washed once with 100 ml of water, dried with magnesium sulphate, filtered and evaporated to dryness. The crude yield is purified over 350 g of silica gel S160 using about 4 l of eluant $CH_2Cl_2$:$CH_3OH$ 99:1. The clean fractions are evaporated to dryness. The crystalline residue is triturated with 100 ml of ether and filtered under suction.

Yield: 11.5 g of grey crystals (50.2% of theory) M.p.: 164°–168° C.

General Procedure III: Cyclisation with Acid Chloride

Example 3

1,3-Dipropyl-8-(4,7,7-trimethyl-2-oxa-bicyclo[2.2.1]-heptan-3-on-1-yl)xanthine 1.2 g (5.4 mmol) of 5,6-diamino-1,3-dipropyluracil and 1.0 g of triethylamine (10 mmol) are dissolved in 50 ml of absolute methylene chloride. After the dropwise addition of 1.2 g (5.5 mmol) of camphanyl chloride, the mixture is stirred for 20 hours at ambient temperature and concentrated by evaporation in vacuo. The residue is mixed with 28 ml of water and 1.7 g of calcium hydroxide and stirred for 3 hours at 80° C. The cooled suspension is acidified whilst being cooled with ice and then extracted with methylene chloride. The combined organic phases are dried and evaporated down and the residue is purified by chromatography on silica gel ($CH_2Cl_2/CH_3OH$ 99:1).

200 mg of the title compound are obtained in the form of white crystals (10% of theory), m.p. 200°–201° C.

General Procedure IV: Vilsmeier Reaction

Example 4

1,3-Dipropyl-8-2-formylfurnan-5-yl)xanthine

At 0°–10° C. 16.4 g (0.11 mol) of phosphorus oxychloride are added dropwise to 400 ml of absolute dimethylformamide. At 5°–15° C. a solution of 15.0 g (0.05 mol) of 1,3-dipropyl-8-furanylxanthine in 330 ml of dimethylformamide is added thereto. The mixture is stirred for 1 hour at ambient temperature and for 7 hours at 85° C. The mixture is poured onto 500 ml of ice and extracted with methylene chloride. The combined organic extracts are dried and evaporated down in vacuo and the residue is crystallised from ether. 12.1 g of the title compound are obtained in the form of brown crystals (73% of theory), m.p. 215°–217° C.

General Procedure V: Oxidation of an Aldehyde to Form the Acid

Example 5

1,3-Dipropyl-8-(2-carboxyfuran-5-yl)xanthine

A solution of 0.26 g (1.5 mmol) of silver nitrate in 2 ml of water is shaken with a solution of 0.4 g of sodium hydroxide in 1 ml of water for 5 minutes. The grey-black silver oxide precipitate is filtered under suction and washed with water, then taken up in 5 ml of water and mixed with 1,3-dipropyl-8-[5-formyl-(2-furanyl)]xanthine. The mixture is heated to 50° C. and a solution of 0.1 g of sodium hydroxide in 2 ml of water is slowly added dropwise. The resulting mixture is stirred for 15 minutes at 50° C. and for 1 hour at ambient temperature and then filtered. The filtrate is acidified and mixed with methylene chloride, the precipitate formed is filtered under suction and washed with methylene chloride and ether. 0.4 g of the title compound are obtained in the form of light brown crystals (77% of theory).

General Procedure VI: Knoevenagel Reaction

Example 6

1,3-Dipropy1-8-[2-(2,2'-bis(ethoxycarbonyl)vinyl)-furan-5-yl]xanthine 2.5 g (7.6 mmol) of 1,3-propyl-dipropyl-8-[5-formyl-(2-furanyl)]xanthine, 1.2 g (7.6 mmol) of diethylmalonate, 0.03 g (0.3 mmol) of piperidine, 0.09 g (1.5 mmol) of glacial acetic acid and 5 ml of benzene p.a. are combined and boiled for 6 hours using a water separator. After the mixture has cooled it is diluted with 10 ml of toluene, the solid matter is suction filtered and dissolved in 100 ml of warm methylene chloride. The solution is filtered, the filtrate is evaporated down in vacuo and the residue is recrystallised from propan-2-ol. 1.0 g of the title compound are obtained in the form of yellow crystals (28% of theory), m.p. 220°–222° C.

General Procedure VII: General Preparation of Amides

Example 7

1,3-Dipropyl-8-[2-(N,N-diethylaminocarbonyl) furan-5-yl]-xanthine 1.0 g (2.9 mmol) of 1,3-dipropyl-8-[2-carboxyfuran-5-yl)]xanthine are dissolved in absolute dimethyl formamide and at 0°–5° C. 0.38 g of triethylamine and 0.45 g (3.3 mmol) of isobutylchloroformate are added thereto. The mixture is stirred for 2 hours at 0°–5° C., then 0.34 g (2.9 mmol) of N,N-diethylamino-ethylamine are added, and the mixture is stirred for approximately a further 12 hours in a thawing ice bath. The mixture is evaporated down in a high vacuum, methylene chloride and water are added, the mixture is made alkaline and extracted with methylene chloride. The organic phases are discarded, the aqueous phase is acidified and extracted once more. The combined organic extracts are dried, filtered and evaporated down and the residue is crystallised from ethyl acetate. 0.25 g of the title compound are obtained in the form of yellowish crystals, m.p. 247°–250° C.

General Procedure VIII: Reduction of a Ketone or Aldehyde to form the Alcohol

Example 8

1,3-Dipropyl-8-(1-hydroxycyclopent-3-yl)xanthine 0.5 g (1.6 mmol) of 1,3-dipropyl-8-(1-oxo-3-cyclopentyl)xanthine, 10 ml of ethanol and 0.1 g (2.6 mmol) of sodium tetrahydridoboranate are stirred for 2½ days at ambient temperature. The mixture is evaporated down, in vacuo and mixed with water and methylene chloride then the aqueous phase is acidified and extracted. The combined organic extracts are dried and evaporated down in vacuo. The residue is separated into the isomers by chromatography on silica gel ($CH_2Cl_2CH_3OH$ 95:5). From the 1st fraction, 0.4 g of the title compound are obtained in the form of white crystals (39% of theory), m.p. 174°–176° C. and from the 2nd fraction 0.4 g of the title compound are obtained in the form of white crystals (39% of theory), m.p. 191°–193° C.

General Procedure IX: Acylation of an Alcohol

Example 9

1,3-Dipropyl-8-[1-((4,7,7-trimethyl-2-oxabicyclo [2.2.1]-heptan-3-on-1-yl)carbonyloxy)cyclopentan-3-yl]xanthine 0.2 g (0.6 mmol) of 1,3-dipropyl-8-(1-hydroxy-3-cyclopentyl)xanthine and 0.24 g (3 mmol) of pyridine are mixed into 10 ml of absolute methylene chloride and after the addition of 0.2 g (0.9 mmol) of camphanyl chloride, the mixture is stirred for 4 hours at ambient temperature. Water is then added and the aqueous phase is separated off. The organic phase is dried and evaporated down in vacuo, then the residue is purified by chromatography on silica gel ($CH_2Cl_2/CH_3OH$ 95:5). 50 mg of the title compound are obtained in the form of a yellowish oil.

General Procedure X: Wittig-Horner Reaction

Example 10

1,3-Dipropyl-8-(1-cyanomethylenecyclopent-3-yl) xanthine 0.28 g (1.6 mmol) of diethylcyanomethane phosphonate are dissolved in 20 ml of absolute benzene and refluxed for 5 hours with 0.13 g (3.2 mmol) of a 60% sodium hydride dispersion. The mixture is evaporated down in vacuo and taken up in methylene chloride and water and then acidified. The aqueous phase is extracted and the combined organic extracts are dried and evaporated down. Subsequent chromatography of the residue on silica gel ($CH_2Cl_2CH_3OH$ 97:3) yields 0.1 g of the title compound in the form of a colourless oil (18% of theory).

General Procedure XI: Hydrogenation of Double Bonds

Example 11

1,3-Dipropyl-8-(norbornan-2-yl)xanthine 1.0 g (3.1 mmol) of 1,3-dipropyl-8-(5-norbornen-2-yl) xanthine are hydrogenated under pressure in 30 ml of ethanol, with the addition of palladium/charcoal, until no further uptake of hydrogen can be detected. The catalyst is filtered off, the filtrate is concentrated by evaporation and the residue is chromatographed on silica gel ($Ch_2Cl_2/CH_3OH$ 99:1). 0.4 g of the title compound are obtained in the form of white crystals (39% of theory), m.p. 136°–138° C.

General Procedure XII: Saponification of an Ester

Example 12

1,3-Dipropyl-8-(2-(2'-ethoxycarbonyl-2'-carboxyvinyl)-furan-5-yl)xanthine 3.2 g (6.8 mmol) of 1,3-dipropyl-8-[2-(2',2'-bis (ethoxycarbonyl)vinyl)-furan-5-yl]xanthine are added to a solution of 0.8 g (1.4 mmol) of potassium hydroxide in 20 ml of ethanol and the mixture is refluxed for 4 hours. After cooling, it is diluted with 50 ml of water and extracted with methylene chloride. The aqueous phase is acidified whilst being cooled with ice and the precipitate formed is filtered off and washed with water. 2.2 g of the title compound are obtained in the form of yellow crystals (73%. of theory), m.p. 252°–253° C.

General Procedure XIII: Reduction of an Ester to Obtain the Alcohol 1.7 mmol of the ester are dissolved in 5 ml of tetrahydrofuran and added dropwise to a suspension of lithium alanate (0.04 g, 1.1 mmol) in 5 ml of tetrahydrofuran. The mixture is stirred at ambient temperature for 36 hours and mixed with saturated diammonium tartrate solution. The aqueous phase is extracted with ethyl acetate, the combined organic extracts are dried and evaporated down in vacuo. The product is purified by crystallisation or by chromatography on silica gel.

General Procedure XIV: N-alkylation

Example 13

1-Benzyl-3-propyl-6-aminouracil 3.0 g (0.014 mol) of 1-benzyl-6-aminouracil are stirred for 3 hours at 70° C. with 2.2 g (0.018 mol) of n-propyl bromide, 4.2 ml of 15% sodium hydroxide solution and 7 ml of ethanol. The mixture is poured onto ice and extracted with methylene chloride. The organic phases are dried and evaporated down. The residual oil is crystallised from a mixture of methylene chloride and methanol. 1.62 g of the title compound are obtained in the form of white crystals (47% of theory), m.p. 189°–192° C.

General Procedure XV: Nitrosation

Example 14

1-Benzyl-3-propyl-5-nitroso-6-aminouracil 2.0 g (7.7 mmol) of 6-amino-1-benzyl-3-propyluracil are heated to 80° C. in 15 ml of water and mixed with a solution of 0.55 g of sodium nitrite in 3 ml of water. After the addition of 1 ml of glacial acetic acid, a red solid is precipitated. The pH is adjusted to 4 and the suspension is stirred for a further 30 minutes at 80° C. After cooling, the crystals are filtered under suction and washed with water. 1.9 g of the title compound are obtained in the form of reddish-violet crystals (86% of theory), m.p. 208°–212° C./decomposition.

General Procedure XVI: Hydrogenation of the Nitroso Compound

The 3-substituted 6-amino-1-benzyl-5-nitrosouracil is taken up in methanol and, after the addition of Raney nickel, hydrogenated under pressure. The catalyst is filtered off, the filtrate is evaporated down and the residue is purified by crystallisation or chromatography.

General Procedure XVII: Etherification

Etherification of alcohols was carried out by deprotonation of the hydroxy function using a strong base (e.g. sodium hydride in tetrahydrofuran or dimethylformamide, sodium hydroxide) and reaction with an electrophile of the type R–X, wherein X may be halogen, tosyl, mesyl or the like.

General Procedure XVIII

Example 15

(+)-1,3-Dipropyl-8-(3-hydroxycyclopentyl)xanthine a) 2.0 g (6.2 mmol) of racemic 1,3-dipropyl-8-(3-hydroxycyclopentyl)xanthine are suspended in 2 l of absolute toluene and mixed with 640 mg of acetic anhydride and 2.0 g of lipase from candidacylindracea, with vigorous stirring. After 6 hours at ambient temperature the enzyme is filtered off and washed with methanol. The combined filtrates are evaporated to dryness in vacuo and the residue is chromatographed with $CH_2Cl_2/CH_3OH$ 95:5 on silica gel.
b) 0.6 g of acetylated product are obtained, which is dissolved in 22 ml of absolute THF and, after the addition of 70 mg of lithium aluminium hydride, stirred for 2 hours at ambient temperature. Whilst the mixture is cooled with ice it is hydrolysed dropwise with 5 ml of $H_2O$, acidified and extracted with methylene chloride. The organic phase is dried and evaporated down and the residue is chromatographed with $CH_2Cl_2/CH_3OH$ 95:5 on silica gel. 490 mg of alcohol are obtained with an optical rotation $[\alpha]_D^{20}=+12°$ (c=0.4, methanol).
c) The optically enriched alcohol is dissolved in 490 ml of absolute methylene chloride and mixed with 490 mg of acetic anhydride and 1.5 g of lipase "Amano P". The mixture is stirred for 24 hours at ambient temperature, filtered to remove the enzyme and the filtrate is evaporated to dryness in vacuo. Chromatography on silica gel using $CH_2Cl_2/CH_3OH$ 95:5 yields 480 mg of alcohol of the title compound with an optical rotation $[\alpha]_D^{20}=+18.2$ (c=0.5, $CH_3OH$); optical purity according to HPLC >99%.

General Procedure XIX

Example 16

(−)-1,3-Dipropyl-8-$C_3$-hydroxy-cyclopentyl) xanthine a) 1.0 g of racemic 1,3-dipropyl-8-(3-hydroxycyclopentyl) xanthine are suspended in 1 l of absolute toluene and stirred with 320 g of acetic anhydride and 1.0 g of lipase from *Candida cylindracea* for 8 hours at ambient temperature. The mixture is filtered to remove the enzyme, then washed with methanol and the filtrates are evaporated to dryness in vacuo. The residue is chromatographed on silica gel using $CH_2Cl_2/CH_3OH$ 95:5. 0.45 g of crystalline residue is obtained, which is then triturated with ether and filtered under suction. This yields 350 mg of crystals with an optical rotation $[\alpha]_D^{20}-13.7$ (c=0.4, $CH_3OH$)
b) The optically enriched alcohol is once again stirred in toluene with 110 mg of acetic anhydride and 350 mg of lipase from Candida cylindracea for 16 hours at ambient temperature. The mixture is worked up as described above. Yield: 200 mg of colourless crystals, optical rotation $[\alpha]_D^{20}=-20.2$ (c=0.5, $CH_3OH$), enantiomeric purity according to HPLC >99.5%.

General Procedure XIX

Example 16

(+) and (−)-1,3-dipropyl-8-(3-oxocyclopentyl) xanthine 1.0 g of optically pure alcohol 28 is dissolved in 30 ml of absolute methylene chloride and after the addition of 1.1 g of pyridinium chlorochromate the mixture is stirred at ambient temperature for 2.5 hours. The mixture is washed twice with $H_2O$, the aqueous phases are extracted with methylene chloride and the combined organic phases are dried and evaporated down in vacuo. Purification is carried out by chromatography on silica gel using $CH_2Cl_2/CH_3OH$ 99:1, 98:2 and 97:3.

Depending on the optically pure alcohol used, the following compounds are obtained.

(+) alcohol yields
(−) 1,3 -dipropyl-8-(3-oxocyclopentyl)xanthine
$[\alpha]_d^{20}-8.3$ (c=0.5, methanol);
(−) alcohol yields
(+) 1,3-Dipropyl-8-(3-oxocyclopentyl)xanthine
$[\alpha]_D^{20}8.0$ (c=0.5 methanol)

The official chemical abstract nomenclature of these compounds is: 8-(3-oxocyclopentyl)-1,3-dipropyl-7H-purin-2,6-dione.

The compounds listed in Table I can be prepared analogously to the procedures described or according to known analogous methods.

TABLE I
| No. | R¹ | R² | R³ | M.pt(°C.) |
|---|---|---|---|---|
| 1 | n-C₃H₇ | n-C₃H₇ | 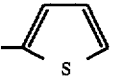 | 272–274 |
| 2 | " | " | 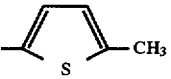 | 276–277 |
| 3 | " | " | 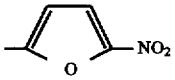 | 258–259 |
| 4 | " | " | 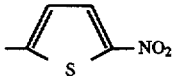 | 283–284 |
| 5 | " | " |  | 262–263 |
| 6 | " | " | 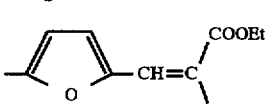 | 220–222 |
| 7 | " | " | 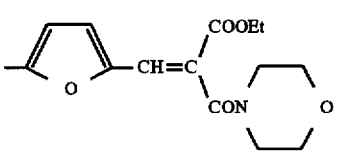 | 252–253 |
| 8 | " | " | 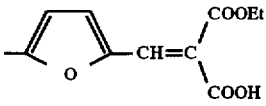 | 252–253 |
| 9 | " | " | 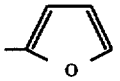 | 255 |
| 10 | " | " | 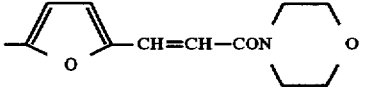 | 253–255 |
| 11 | n-C₃H₇ | n-C₃H₇ |  | 247–250 |
| 12 | " | " | 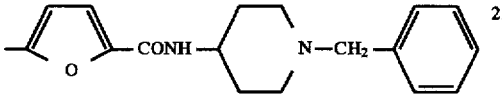 | 210–217 |
| 13 | " | " | 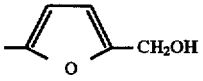 | 235–236 |
| 14 | " | " | 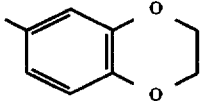 | 280–282 |
| 15 | " | " | 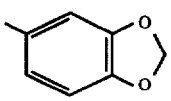 | 291–294 |

TABLE I-continued
| No. | R¹ | R² | R³ | M.pt(°C.) |
|---|---|---|---|---|
| 16 | " | " | 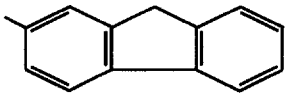 | >300 |
| 17 | " | " | 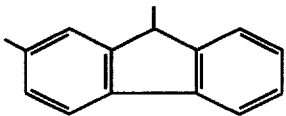 | 228–229 |
| 18 | CH₃ | CH₃ | 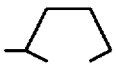 | 228–230 |
| 19 | CH₃ | CH₃ | 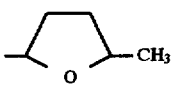 | 148–150 |
| 20 | n-C₃H₇ | n-C₃H₇ | 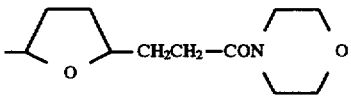 | 135–137 |
| 21 | " | " | 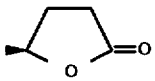 | 195–196 |
| 22 | " | " | 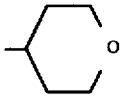 | 171–172 |
| 23 | CH₃ | CH₃ | 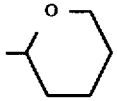 | 275–277 |
| 24 | n-C₃H₇ | n-C₃H₇ | 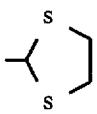 | 213–213 |
| 25 | " | " | 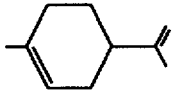 | 205–207 |
| 26 | " | " |  | 197–198 |
| 27 | " | " |  | 80–83 |
| 28 | " | " |  | 186–187 |

TABLE I-continued

| No. | R¹ | R² | R³ | M.pt(°C.) |
|---|---|---|---|---|
| 29 | $CH_3$ | $CH_3$ | cyclohexyl | 260 |
| 30 | $n-C_3H_7$ | $n-C_3H_7$ | cyclohexenyl | 179–181 |
| 31 | " | " | 1,3-dithian-2-yl | 197–198 |
| 32 | $CH_3$ | $CH_3$ | cyclohexenyl | 273–275 |
| 33 | $n-C_3H_7$ | $n-C_3H_7$ | 3-oxocyclopentyl | 165–167 |
| 34 | " | " | 4-oxocyclohexyl | 138–140 |
| 35 | $CH_3$ | $CH_3$ | 4-oxocyclohexyl | 292 |
| 36 | " | " | 3-oxocyclohexyl | |
| 37 | $n-C_4H_9$ | $n-C_4H_9$ | 3-oxocyclohexyl | 142–150 |
| 38 | $CH_3$ | $CH_3$ | 3-oxocyclopentyl | 292 |
| 39 | $n-C_3H_7$ | $n-C_3H_7$ | 3-hydroxycyclopentyl (α-OH) | 174–176 |
| 40 | " | " | 3-hydroxycyclopentyl (β-OH) | 191–193 |
| 41 | $CH_3$ | $CH_3$ | 4-hydroxycyclohexyl | 277–280 |
| 42 | $n-C_3H_7$ | $n-C_3H_7$ | =CH—COOCH₃ cyclopentylidene | 213–216 |
| 43 | " | " | cyclopentyl-OC(O)-camphanic acid | 101–112 |

TABLE I-continued

| No. | R¹ | R² | R³ | M.pt(°C.) |
|---|---|---|---|---|
| 44 | " | " | (norbornene) | 156–157 |
| 45 | " | " | (norbornene) | 166–168 |
| 46 | " | " | cyclopentyl-OC(=O)CH₃ | 144–148 |
| 47 | " | " | cyclopentyl(OH)(CH₃) | 151–152 |
| 48 | " | " | cyclopentyl-CH₂COOCH₃ | 146–147 |
| 49 | " | " | (norbornene) | 137–139 |
| 50 | " | " | (norbornene) | 136–138 |
| 51 | " | " | camphor-like | 200–201 |
| 52 | " | " | tetrahydrofuranyl | 162 |
| 53 | " | " | tetrahydrofuranyl | 180 |
| 54 | " | " | cyclopentyl-CH₂CH₂OH | 164–165 |
| 55 | " | " | cyclopentyl-OC(=O)CH₂O-menthyl | 134–135 |
| 56 | " | " | cyclopentyl-OC(=O)-phenyl | 148–151 |

TABLE I-continued

| No. | R¹ | R² | R³ | M.pt(°C.) |
|-----|----|----|-----|-----------|
| 57 | " | " | cyclopentyl-methyl =CH-CN | 126–147 |
| 58 | " | " | cyclopentyl-CH₂CH₂NH₂ | 199–203 |
| 59 | " | " | cyclopentyl-OC(C₆H₅)₃ | 166–168 |
| 60 | " | " | cyclopentyl spiro 1,3-dioxolane | 155–157 |
| 61 | " | " | cyclopentyl-OH, (CH₂)₂CH₃ | 83–85 |
| 62 | " | " | cyclopentyl-OCO-pyridyl | 202–205 |
| 63 | " | " | cyclopentyl-OH, C₆H₅ | 130–133 |
| 64 | " | " | cyclopentyl-OH, C(CH₃)₃ | 124–127 |
| 65 | " | " | cyclopentyl-OCO-NHC₆H₅ | 210–213 |
| 66 | " | " | cyclopentyl =N—NH-(2,4-dinitrophenyl) | 256–259 |
| 67 | " | " | cyclopentyl =CH₂ | 170–173 |
| 68 | " | " | cyclopentyl-OC(=O)-pyridyl | 185–186 |
| 69 | " | " | cyclopentyl-H, CH₃ | 181–182 |
| 70 | " | " | cyclopentyl-H, CH₂OH | 196–198 / 173–175 |

TABLE I-continued

| No. | R¹ | R² | R³ | M.pt(°C.) |
|---|---|---|---|---|
| 71 | " | " | cyclopentyl–OC(=O)–C₆H₂(OMe)₃ (2,3,4-trimethoxybenzoate) | 162–164 |
| 72 | " | " | cyclopentyl–OCH₃ | 153–154 |
| 73 | " | " | cyclopentyl–OC(=O)–pyridyl | 155–156 |
| 74 | " | " | cyclopentyl =NOH | 234–236 |
| 75 | " | " | cyclopentyl =O (S) | 172–173 |
| 76 | " | " | cyclopentyl =O (R) | 174–175 |
| 77 | " | " | cyclopentyl –OH (SS) | 188–189 |
| 78 | " | " | cyclopentyl –OH (RR) | 182–183 |

The compounds of general formula (I) may be used either on their own or in conjunction with other active substances according to the invention, possibly in conjunction with other pharmacologically active substances. Suitable forms for administration include, for example, plain or coated tablets, capsules, suppositories, solutions, syrups, emulsions or dispersible powders. Tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release such as carboxymethylcellulose, cellulose acetate phthalate or polyvinyl acetate. The tablets may also consist of several layers.

Coated tablets may be produced accordingly by coating cores made in the same way as the tablets with the substances normally used for tablet coating, such as collidone or shellac, gum arabic, talc, titanium dioxide or sugar. In order to obtain delayed release or prevent incompatibilities, the core may also consist of several layers.. Similarly, the tablet coating may consist of several layers in order to obtain delayed release, and the excipients mentioned above for the tablets may be used.

Syrups of the active substances or combinations of active substances according to the invention may additionally contain a sweetener such as saccharin, cyclamate, glycerol or sugar and a flavour-enhancing agent, e.g. a flavouring such as vanillin or orange extract.

They may also contain suspension adjutants or thickeners such as sodium carboxymethylcellulose, wetting agents, e.g. condensation products of fatty alcohols with ethylene oxide, or preservatives such as p-hydroxybenzoates.

Injection solutions are prepared in the usual way, e.g. by adding perservatives such as p-hydroxybenzoates or stabilizers such as alkali metal salts of ethylenediaminetetraacetic acid and the resulting solutions are transferred into injection vials or ampoules.

Capsules containing one or more active substances or combinations of active substances may be prepared, for example, by mixing the active substances with inert carriers such as lactose or sorbitol and encapsulating the mixture in gelatine capsules.

Suitable suppositories may be produced, for example, by mixing the active substances or combinations of active substances envisaged therefore with conventional carriers such as neutral fats or polyethylene glycol or the derivatives thereof.

The Examples which follow illustrate the invention without restricting its scope:

Examples of pharmaceutical formulations

| A) Tablets | per tablet |
|---|---|
| Active substance | 100 mg |
| Lactose | 140 mg |
| Corn starch | 240 mg |
| Polyvinylpyrrolidone | 15 mg |
| Magnesium stearate | 5 mg |
| | 500 mg |

The finely ground active substance, lactose and some of the corn starch are mixed together. The mixture is screened, then moistened with a solution of polyvinylpyrrolidone in water, kneaded, granulated whilst wet and dried. The granulate, the remaining corn starch and the magnesium stearate are screened and mixed together. The mixture is compressed to form tablets of suitable shape and size.

| B) Tablets | per tablet |
|---|---|
| Active substance | 80 mg |
| Corn starch | 190 mg |
| Lactose | 55 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active substance, some of the corn starch, lactose, microcrystalline cellulose and polyvinylpyrrolidone are mixed together, the mixture is screened and combined with the remaining corn starch and water to form granules which are dried and screened. The sodium carboxymethyl starch and magnesium stearate are added and thoroughly mixed and the mixture is compressed to form tablets of suitable size.

We claim:

1. The compound 1,3-di-n-propyl-8-(5-norbornen-2-yl) xanthine.

2. A pharmaceutical composition comprising the compound according to claim 1 or a physiologically acceptable acid addition salt thereof and a conventional excipient or carrier.

3. A method for the systemic treatment of senile dementia, Alzheimer's disease, organic brain syndrome, or Parkinson's disease, comprising the step of administering to a host suffering from one of said conditions a therapeutically effective amount of the pharmaceutical composition according to claim 2.

* * * * *